US008768657B2

(12) United States Patent
Goldfine et al.

(10) Patent No.: US 8,768,657 B2
(45) Date of Patent: Jul. 1, 2014

(54) REMAINING LIFE PREDICTION FOR INDIVIDUAL COMPONENTS FROM SPARSE DATA

(75) Inventors: Neil J. Goldfine, Newton, MA (US); Vladimir A. Zilberstein, Chestnut Hill, MA (US); Volker Weiss, Syracuse, NY (US); Yanko K. Sheiretov, Waltham, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 400 days.

(21) Appl. No.: 11/653,067

(22) Filed: Jan. 12, 2007

(65) Prior Publication Data

US 2007/0239407 A1   Oct. 11, 2007

Related U.S. Application Data

(60) Provisional application No. 60/758,665, filed on Jan. 12, 2006, provisional application No. 60/856,081, filed on Nov. 2, 2006.

(51) Int. Cl.
| | |
|---|---|
| G06F 7/60 | (2006.01) |
| G06F 17/10 | (2006.01) |
| G06F 19/00 | (2011.01) |
| G21C 17/00 | (2006.01) |
| G06F 15/18 | (2006.01) |
| G06E 1/00 | (2006.01) |
| G06E 3/00 | (2006.01) |
| G06G 7/00 | (2006.01) |
| G01N 27/82 | (2006.01) |
| G06N 7/00 | (2006.01) |
| G01B 7/34 | (2006.01) |

(52) U.S. Cl.
CPC .............. G01N 27/82 (2013.01); *G06N 7/005* (2013.01); *G01B 7/34* (2013.01)
USPC ................................. 703/2; 702/183; 706/21

(58) Field of Classification Search
CPC ........... G01N 27/82; G06N 7/005; G01B 7/34

USPC .......... 703/2; 707/101, 102; 706/21; 702/183
See application file for complete search history.

(56) References Cited

U.S. PATENT DOCUMENTS

| 4,175,447 A | 11/1979 | Fukuhara |
|---|---|---|
| 4,574,642 A | 3/1986 | Fleischman |

(Continued)

OTHER PUBLICATIONS

Timothy D. Righiniotis, Mairos K. Chryssanthopoulos, "Fatigue and fracture simulation of welded bridge details through a bi-linear crack growth law", May 16, 2003, Elsevier, Structural Safety 26(2004) 141-158.*

(Continued)

*Primary Examiner* — Omar Fernandez Rivas
*Assistant Examiner* — Angel Calle
(74) *Attorney, Agent, or Firm* — Hamilton, Brook, Smith & Reynolds, P.C.

(57) ABSTRACT

Predicting the remaining life of individual aircraft, fleets of aircraft, aircraft components and subpopulations of these components. This is accomplished through the use of precomputed databases of response that are generated from a model for the nonlinear system behavior prior to the time that decisions need to be made concerning the disposition of the system. The database is calibrated with a few data points, to account for unmodeled system variables, and then used with an input variable to predict future system behavior. These methods also permit identification of the root causes for observed system behavior. The use of the response databases also permits rapid estimations of uncertainty estimates for the system behavior, such as remaining life estimates, particularly, when subsets of an input variable distribution are passed through the database and scaled appropriately to construct the output distribution. A specific example is the prediction of remaining life for an aircraft component where the model calculates damage evolution, input variables are a crack size and the number of cycles, and the predicted parameters are the actual stress on the component and the remaining life.

27 Claims, 11 Drawing Sheets

(56) References Cited

U.S. PATENT DOCUMENTS

| | | | |
|---|---|---|---|
| 5,047,719 A | 9/1991 | Johnson et al. | |
| 5,262,722 A | 11/1993 | Hedengren et al. | |
| 5,278,498 A | 1/1994 | Vernon et al. | |
| 5,315,234 A | 5/1994 | Sutton, Jr. et al. | |
| 5,371,462 A | 12/1994 | Hedengren et al. | |
| 5,453,689 A | 9/1995 | Goldfine et al. | |
| 5,793,206 A | 8/1998 | Goldfine et al. | |
| 5,966,011 A | 10/1999 | Goldfine et al. | |
| 6,144,206 A | 11/2000 | Goldfine et al. | |
| 6,188,218 B1 | 2/2001 | Goldfine et al. | |
| 6,198,279 B1 | 3/2001 | Goldfine et al. | |
| 6,226,597 B1 | 5/2001 | Eastman et al. | |
| 6,351,120 B2 | 2/2002 | Goldfine et al. | |
| 6,377,039 B1 | 4/2002 | Goldfine et al. | |
| 6,380,747 B1 | 4/2002 | Goldfine et al. | |
| 6,420,867 B1 | 7/2002 | Goldfine et al. | |
| 6,486,673 B1 | 11/2002 | Goldfine et al. | |
| 6,636,813 B1 | 10/2003 | Isobe et al. | |
| 6,657,429 B1 | 12/2003 | Goldfine et al. | |
| 6,727,691 B2 | 4/2004 | Goldfine et al. | |
| 6,781,387 B2 | 8/2004 | Goldfine et al. | |
| 6,784,662 B2* | 8/2004 | Schlicker et al. | 324/242 |
| 6,798,198 B2 | 9/2004 | Tsukernik et al. | |
| 6,952,095 B1 | 10/2005 | Goldfine et al. | |
| 6,992,482 B2 | 1/2006 | Shay et al. | |
| 6,995,557 B2 | 2/2006 | Goldfine et al. | |
| 7,006,947 B2 | 2/2006 | Tryon, III et al. | |
| 7,049,811 B2 | 5/2006 | Schlicker et al. | |
| RE39,206 E | 7/2006 | Goldfine et al. | |
| 7,095,224 B2 | 8/2006 | Goldfine et al. | |
| 7,106,055 B2 | 9/2006 | Goldfine et al. | |
| 7,107,491 B2 | 9/2006 | Graichen et al. | |
| 7,161,350 B2 | 1/2007 | Goldfine et al. | |
| 7,161,351 B2 | 1/2007 | Goldfine et al. | |
| 7,183,764 B2 | 2/2007 | Goldfine et al. | |
| 7,188,532 B2 | 3/2007 | Goldfine et al. | |
| 7,230,421 B2 | 6/2007 | Goldfine et al. | |
| 7,280,940 B2 | 10/2007 | Goldfine et al. | |
| 7,348,771 B2 | 3/2008 | Goldfine et al. | |
| 7,385,392 B2 | 6/2008 | Schlicker et al. | |
| 7,411,390 B2 | 8/2008 | Goldfine et al. | |
| 7,451,639 B2 | 11/2008 | Goldfine et al. | |
| 7,451,657 B2 | 11/2008 | Goldfine et al. | |
| 7,467,057 B2 | 12/2008 | Sheiretov et al. | |
| 7,518,360 B2 | 4/2009 | Goldfine et al. | |
| 7,526,964 B2 | 5/2009 | Goldfine et al. | |
| 7,528,598 B2 | 5/2009 | Goldfine et al. | |
| 7,634,383 B2* | 12/2009 | Engel et al. | 702/181 |
| 8,494,810 B2 | 7/2013 | Goldfine et al. | |
| 2003/0025497 A1 | 2/2003 | Collingwood et al. | |
| 2003/0154052 A1 | 8/2003 | Samata et al. | |
| 2003/0164700 A1 | 9/2003 | Goldfine et al. | |
| 2004/0167756 A1* | 8/2004 | Yonezawa | 703/2 |
| 2004/0225474 A1* | 11/2004 | Goldfine et al. | 702/183 |
| 2004/0232911 A1* | 11/2004 | Schlicker et al. | 324/242 |
| 2005/0096873 A1 | 5/2005 | Klein | |
| 2005/0146324 A1* | 7/2005 | Goldfine et al. | 324/238 |
| 2006/0009923 A1 | 1/2006 | Shay et al. | |
| 2006/0265261 A1 | 11/2006 | Wetzer et al. | |
| 2007/0069720 A1* | 3/2007 | Goldfine et al. | 324/240 |
| 2007/0236214 A1 | 10/2007 | Goldfine et al. | |
| 2008/0177516 A1 | 7/2008 | Vasudevan et al. | |
| 2008/0289423 A1 | 11/2008 | Gordon et al. | |
| 2009/0037122 A1* | 2/2009 | Engel et al. | 702/35 |
| 2010/0082267 A1 | 4/2010 | Schimert et al. | |
| 2010/0106430 A1 | 4/2010 | Balestra | |

OTHER PUBLICATIONS

Shalabh Gupta, Dheeraj S. Singh, and Asok Ray, "Statistical pattern analysis of ultrasonic signals for fatigue damage detection iin mechanical structures", 2008.*

Wolfram Burgard, Dieter Fox, Daniel Hennig and Timo Schmidt, "Estimating the Absolute Position of a Mobile Robot using Position Probability Grids", AAAI-96, Citeseer, 1996.*

V. Zilberstein, D. Grundy, "Early detection and monitoring of fatigue in high strength steels with MWM-Arrays", Sep. 2005.*

Neil Goldfine, Vladimir Zilberstein, Andrew Washabaugh, "Eddy Current Sensor Network for Aircraft Fatigue Monitoring", Jul. 2003.*

Rooke, D.P., and Cartwright, D.J., Compendium of Stress Intensity Factors, pp. 158-159, 1976.

Goldfine, N., Windoloski, M., Zilberstein,V., Contag, G., N. Phan, R. Davis, "Mapping & Tracking of Damage in Titanium Components for Adaptive Life Management," $10^{th}$ Joint NASA/DoD/ FAA Conference on Aging Aircraft, Atlanta, GA; Apr. 16-20, 2007.

Goldfine, N., Grundy, D., Washabaugh, A., Zilberstein, V., Weiss, V., Davis, M., Schaff, J., Hullander, T., Davis, W., Contag, G., Timmons, A., Hardman, B., "Damage and Usage Monitoring for Vertical Flight Vehicles," American Helicopter Society (AHS) $63^{rd}$ Annual Forum and Technology Display; Virginia Beach, Virginia; May 1-3, 2007.

Goldfine, N., Sheiretov, Y., Washabaugh, A., Zilberstein, V., Jablonski, D., Contag, G., "Sensing and Risk Assessment for Condition Based Maintenance 'Plus' ", $12^{th}$ Joint FAA/DoD/NASA Conference on Aging Aircraft, Kansas City, MO. May 4-9, 2009.

Goldfine, N., Grundy, D., Jablonski, D., Zilberstein, V., "Automated Fatigue Test Monitoring and Damage Evolution Tracking for Prognosis in Support of Condition Based Maintenance Decisions—Part I: Fatigue Tests," ASM AeroMat, Dayton, OH, Jun. 7-10, 2009.

Goldfine, N., Denenberg, S., Lyons, R., Sheiretov, Y., Washabaugh, A., "Automated Fatigue Test Monitoring and Damage Evolution Tracking for Prognosis in Support of Condition Based Maintenance Decisions—Part II: Prognosis," ASM AeroMat, Dayton, OH, Jun. 7-10, 2009.

Goldfine, N., "Remaining Life Prediction for Individual Components from Sparse Data (for CBM+)," Navy Opportunity Forum, Arlington, VA, Jun. 7-10, 2009.

Office Action dated Sep. 4, 2012 for U.S. Appl. No. 12/795,538.

Mohanty, et al., "Off-Line and On-Line Fatigue Crack Growth Prediction Using Multivariate Gaussian Process," Submitted to AIAA Journal in 2008 24 pages.

Notice of Allowance dated Mar. 22, 2013 for U.S. Appl. No. 12/795,538.

U.S. non-final Office Action dated May 14, 2012 for U.S. Appl. No. 12/795,561.

* cited by examiner

REMAINING LIFE PREDICTION FOR INDIVIDUAL COMPONENTS FROM SPARSE DATA

RELATED APPLICATIONS

This application claims the benefit of U.S. Provisional Application No. U.S. Provisional Application Nos. 60/758,665 filed on Jan. 12, 2006 and 60/856,081 filed on Nov. 2, 2006. The entire teachings of the above applications are incorporated herein by reference.

BACKGROUND OF THE INVENTION

The technical field of this invention is life cycle management. Current practice of life cycle management of critical components for high value assets such as aircraft and rotorcraft fall into three categories: damage tolerance, safe-life and fail-safe. Each of these methods requires reliable predictions of damage evolution behavior to enable practical application. When mission requirements change during service, uncertainties in model inputs are substantial, or damage behavior mechanisms are not well understood, for example for advanced materials such as composites, it is difficult to predict damage evolution behavior. These traditional methods for life cycle management provide limited value. Furthermore, even when such models capture a substantial portion of the relevant behavior, calculations of uncertainties in sufficient time to support interactive decisions by owners, maintainers and operators are often extremely time consuming.

A common part of the life cycle management methods is the use of Nondestructive evaluation (NDE) methods. NDE methods provide information about near-surface, and bulk material condition for flat and curved parts or components. These methods can include periodic inspections as well as usage monitoring with onboard diagnostics. This information is then used in a condition based maintenance or prognostic health management programs to extend the service life of a variety of systems, such as engines and aircraft.

NDE of legacy and new aircraft platforms, performed at the depot or in the field, have a goal to reduce sustainment costs while maintaining a high level of safety and operational readiness. While inspections of fatigue critical locations may be performed to try to assess the damage, such as the presence of cracks, these inspections are often difficult and costly. Even with embeddable sensors the data recording may not be continuous during flight, since it is often more practical to connect to such sensors periodically to record damage/condition data than to fly instrumentation on-board for continuous monitoring. Thus, damage state data from such sensors is often sparse to reduce the impact on aircraft availability and costs. Similarly, existing damage tolerance methods use predictive tools for crack growth to set NDE inspection intervals, to reduce premature component retirements. These damage tolerance methodologies assume an initial crack size, just below the detection threshold of available NDE methods. Inspection intervals are then set at a fraction of the time it takes for the assumed initial crack to reach this critical crack size.

There are a number of difficulties with the damage tolerance approach. One is the typically lengthy time required to run the models for predicting cracks growth. A second is the substantial variation in crack initiation and growth behavior, even at essentially identical features on components. This uncertainty can limit the usefulness of the predictive models. A third is rapid crack growth, inherent in many dynamic components, which begins before conventional NDE methods can provide reliable crack detection. Since this information is needed by the damage tolerance method, it again can limit the usefulness of the predictive models.

Advanced NDE sensors suitable for inspection or monitoring of difficult-to-access locations are flexible and conformable eddy current sensors. Examples of such conformable sensors are described, for example, by Goldfine (U.S. Pat. No. 5,453,689), Vernon (U.S. Pat. No. 5,278,498), Hedengren (U.S. Pat. No. 5,315,234) and Johnson (U.S. Pat. No. 5,047,719). These sensors permit characterization of bulk and surface material conditions. Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks, cracks or stress variations in magnitude, orientation or distribution.

Conventional eddy-current sensing involves the excitation of a conducting winding, the primary, with an electric current source of prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

SUMMARY OF THE INVENTION

Aspects of the methods described herein involve nondestructive evaluation of life cycle management of high value assets and individual components using both damage evolution predictions and root cause identification for observed behaviors.

In one embodiment, a decision concerning the disposition of a system, such as rework, repair or replace a high value asset or component, uses a precomputed database of responses that were generated by a model. The model needs capture enough of the nonlinear behavior for the system to allow reasonably accurate estimates of future behavior. The database is generated prior to the time when the decision needs to be made concerning the system and has at least two input variables. In embodiments, the model is a damage evolution model. Example embodiments of the input variables include a crack size, such as length or depth, and the number of cycles. This database is calibrated using empirical information about the system, where the calibration adjusts the database to reflect differences between the model and actual system. In an embodiment, the information is sensor based and uses an eddy current sensor. After calibration, an input value is used for one of the input variables, such as the number of cycles, passed through the database so that a multivariate inverse method converts the input into a system response value, and then the system response value is used to make the decision. Representative system response values are the remaining life for the system and a prediction for future system behavior.

In another embodiment, the multivariate inverse method is used to obtain addition information about the system. This can include identification of root cause variables, such as residual stress, applied load amplitude, or shot peen levels, and estimating a value for this unknown input. It can also include determining an uncertainty for the system response value by using a distribution in values for an input variable. In embodiments, the input variable distribution can be assumed or measured. In specific embodiments, the system is a shot peened material or the system response is an image of effective material properties. Furthermore, tracking of the system response value for multiple input values allows refinement or upgrades for one or more of the model inputs or calibration.

In yet another embodiment, a database of responses is used to estimate an output value distribution for a system. The database is in the form of a hypercube that relates at least two input variables to at least one output value. A distribution, or an uncertainty distribution, is also provided for at least one of the input variables. The distribution is compartmentalized or divided into multiple portions and a weighting value is determined for each portion based on the distribution. This information is then used in combination with the databases to calculate a mean output value and the output value distribution. Preferably, the database is generated from a model for the system behavior prior to the use of the database in determining the output value distribution. In embodiments, the input distribution is in terms of a quantitative distribution function or a probability density function. In an embodiment, this calculation is performed efficiently using a portion of the input variables and distribution value, preferably using a Latin hypercube methodology.

A method for estimating an output value distribution for a system is also disclosed. The method comprising providing a database of system responses, the database relating a plurality of input variables to at least one output value, providing the input variables to the system with an uncertainty distribution for at least one variable, dividing the uncertainty distribution into portions, determining a weighting value for each portion, and calculating an output value distribution by passing the input variables and each weighted value of the uncertainty distribution through the database.

A method for rapid decision making for a nonlinear system is also disclosed. The method comprising generating a database of system responses from a model, with the responses having a nonlinear dependence on at least two input variables, storing the database for future use, calibrating the database with empirical information about the system, obtaining an input value for an input variable, converting the input value into a system response value using the database and a multivariate inverse method, and using the system response value to make a decision.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
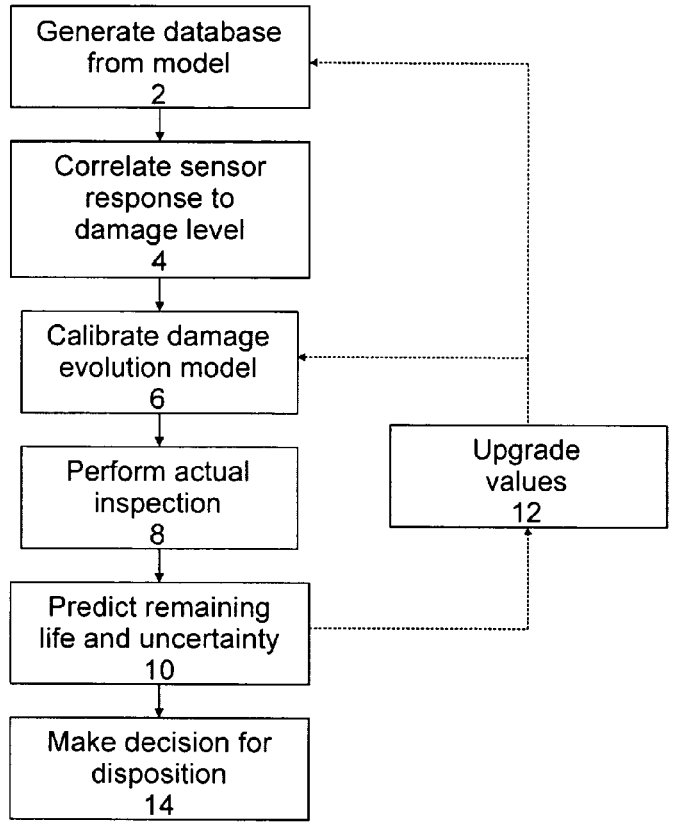
FIG. 1 shows a schematic diagram for remaining life prediction.

A description of preferred embodiments of the invention follows. The disclosed invention addresses the need for remaining life prediction, root cause identification and rapid uncertainty estimation tools for individual aircraft, fleets of aircraft, aircraft components and populations and subpopulations of aircraft components. In one embodiment, this tool incorporates early stage damage detection data, which is typically relatively sparse, precomputed databases of damage evolution modeled responses, and calibration of the model based on both the sparse in-service data and laboratory data, to provide rapid predictions for damage evolution and for identification of root causes for the observed damage evolution behaviors. While the following focus is on aircraft, the approach is suitable for other systems where the behavior is nonlinear and a model can be used to predict the future behavior for the system, but only limited or sparse data is available. Furthermore, this invention can be applied to processes and systems for which anomalous behavior is observed due to faulty operation that is described by nonlinear behaviors that can be modeled with sufficient accuracy. This invention is most valuable for behaviors that can be modeled with overall accuracies in the 30 to 90% range. If the accuracy is higher than 90% over the entire range of interest then predictions without recalibration and uncertainty estimations may be sufficient for practical use. If the modeling accuracy is less than 30% the behaviors may not be sufficiently modeled to justify the computational burden of this disclosed approach.

Often the actual usage of individual components is different than what was initially intended, which can compromise safety. Thus, remaining life prediction tools must capture the actual experience of each individual component to take advantage of the potential cost savings without reducing safety margins. Equally important, however, is the need to identify root causes of early failures. If for example, early failures are caused by the variability in a manufacturing process, such as poor shot peening quality or surface finish, by an unanticipated random even, such as an overload or foreign object damage, or by a difference in the assumed and actual mission load spectrum then individual failures must be analyzed to isolate the root cause. This is critical to implementation of a useful individual component life management methodology.

Although reducing conservatism for some populations of components may be worthwhile, tailoring solutions to individual component usage is better. However, this requires improved observability of individual component damage and enhanced monitoring of individual component usage (loads); it also requires a method for determining model inputs and calibrating models of damage evolution based on individual component observations from limited empirical data (from coupons, subcomponents, test aircraft and failed/retired components), as well as sparse data from inspections of the actual component.

FIG. 1 shows a schematic representation of one embodiment of the disclosed life prediction tool. This includes generating a precomputed database 2 of damage evolution response curves, establishing a correlation 4 between the sensor response and damage level (typically with coupon studies), calibrating 6 or validating the damage evolution model (typically with subcomponent or component tests), performing actual in-service part inspection 8 and monitoring, and predicting the remaining life 10. An important part of the remaining life prediction is the prediction of failure probability distributions. Other decisions 14 can then be made based on this information, such as the airworthiness of the aircraft and maintenance rework/repair/replace decisions. This information can also be used for fleetwide population tracking and tracking of subpopulations (for example from one manufacturer, from a class of manufacturing parameters, from different mission spectrum classes or from geographic deployment subclasses) and learning from the observed damage. It may also be used to upgrade 12 the model assumptions and values for regeneration of databases and also revisions to the calibration.

Figure 2:
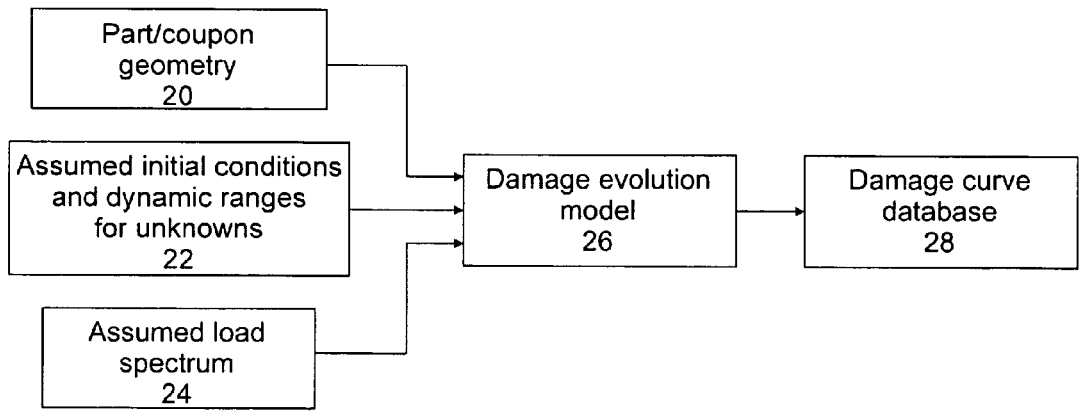
FIG. 2 illustrate damage evolution model inputs and generation of damage trajectories for precomputed database generation.

FIG. 2 illustrate the generation of a precomputed database of damage evolution response surfaces. In this case a damage evolution model 26 has inputs including the part/coupon geometry 20, assumed initial conditions and dynamic ranges for unknown parameter values 24, and an assumed load spectrum 24. Representative initial conditions include initial crack sizes and residual stresses. Representative unknown parameters include surface roughness, the largest inclusion in a region of interest, and microstructure variations. The output of the damage evolution model is a database 28 of damage trajectories at each location that can be stored as a function of the remaining life, cycles, or flight hours. In this case the damage evolution database is a function of flight hours and position along the part surface, for the range of model input parameters and load spectra of interest. The procedure involved selecting the forward model, defining assumed parameter values, identifying critical model unknowns, assuming load spectrum parameters, running a model for all possible unknown combinations, and storing the results in a database format. These databases are in a form that relates the known values to those that are to be determined. In two-dimensions these databases can be visualized as "grids" that relate two measured parameters to two unknowns. Three- (or more)-dimensional versions of these grids called lattices and hypercubes, respectively, can be used for the determination of additional values for the system being modeled.

For establishing a correlation between the sensor response and damage level, tests need to be performed on a statistically sufficient set of coupons and subcomponents. Each test needs to be stopped periodically with a range of pre-selected damage levels with scans performed to examine the test material for damage, such as with a scanning electron microscope. This may also include destructive examination of the coupons. Then a correlation function is generated that relates sensor response to damage level, such as effective flaw size, plastic deformation from overload, or another damage characteristic. The uncertainty in the correlation function and detection probability as a function of damage level also needs to be determined.

For calibrating or validating the damage evolution model, at least two coupon tests are run with different combination of initial conditions, such as residual stress, initial crack size, roughness, or overload. Then, using the previously generated correlation function and the precomputed database of responses, model scale factors, offsets, and assumed parameters can be adjusted to achieve a best fit to the coupon responses. The databases can be rescaled or regenerate for new assumed known input values. The model assumptions are then verified or validated using quantitative metrics on damage evolution, with the model assumption confidence levels also being determined. Note that these steps of database generation, correlation function generation, and calibration are interactive, requiring human input, and iterative until acceptable confidence levels are reached for model and calibration validation/verification.

For actual in-service part with adaptive inspection scheduling, additional tests are performed. These tests may also be performed on coupons or components. These tests require baseline measurements to determine initial conditions and uncertainties in these initial conditions. Then NDE inspection data is provided or downloaded from embedded sensors at predetermined intervals.

For predicting the remaining life, multivariate inversions are performed. This is a multidimensional table look-up from the precomputed database of responses, but other numerical methods for searching through the database can also be performed. For example, standard numerical methods such as iterative methods that minimize the least-squares error between the predicted and known responses can be used. These approaches may also use singular value decomposition or other representations of the Jacobian for the system model. As another example, the database searching can be performed using a unified mathematical environment where efficient building blocks (cubes, simples, etc.) are used to represent the solution space. This inversion includes data from the current time but can also include historical data at each sensor or sensing element location. The model is then used with the revised initial conditions to predict damage evolution to the end of life. This may also be used to adjust the inspection intervals based on the damage evolution so that the predetermined intervals for the in-service part are updated to reflect this new information. This updating of the intervals is in the form of an adaptive feedback loop.

The uncertainty in the remaining life or the distribution of the remaining life estimates is also determined with the precomputed database or hypercube of model responses. An efficient method for doing this is to use a Latin hypercube methodology where only a fraction of the input distribution is passed through the precomputed database to reconstruct the distribution of the output. This approach for obtaining the output distribution involves taking a Gaussian distribution or other distribution for the input, dividing it into equal width compartments, running one data point in each compartment through the precomputed database, and scaling the output by the size of the compartment in the input. This scaling of the output is effectively a weighting factor for each compartment. As opposed to running a Monte Carlo simulation, this requires a substantially reduced number of cases to be run through the database to construct the output distribution. For example, only ten compartments can be used to reconstruct the output distribution.

Note that on complex-shape parts, fatigue damage often manifests itself as a varying spatial distribution of measured properties in the monitored areas of interest. Comparison of these spatial distributions and damage trajectory tracking at each location enhances life prediction estimates and also improves early damage observability confidence levels. This also applies to single-location damage evolution for coupons. This mapping and tracking of damage evolution, in one embodiment, uses a high resolution MWM-Array to first baseline the properties of a metallic component, for example a shot peened titanium engine component. Then successive time sequenced images are recorded with the same sensor. These images are filtered using conventional or novel space-time filtering methods to enhance damage evolution behaviors and suppress noise and inconsequential behaviors. Quantitative features from these filtered images are then used as inputs to the remaining life prediction or root cause identification algorithms. For the shot peen example, residual stress relaxation in titanium is observed using a unidirectional MWM-Array conductivity image to determine if shot peen stresses have relaxed, resulting in a significant reduction in remaining life. This prediction of a reduction in remaining life for an individual component is then used to prompt on-condition maintenance. The results of such maps from a sub-population of components can also be used to identify a root cause, for example a geometric misalignment for a statistically significant portion of a dynamic component population. The patterns of such maps being used to diagnose the geometric misalignment, is then feedback to the original equipment manufacturer (OEM) or maintainers to devise a remediation action.

Figure 3:
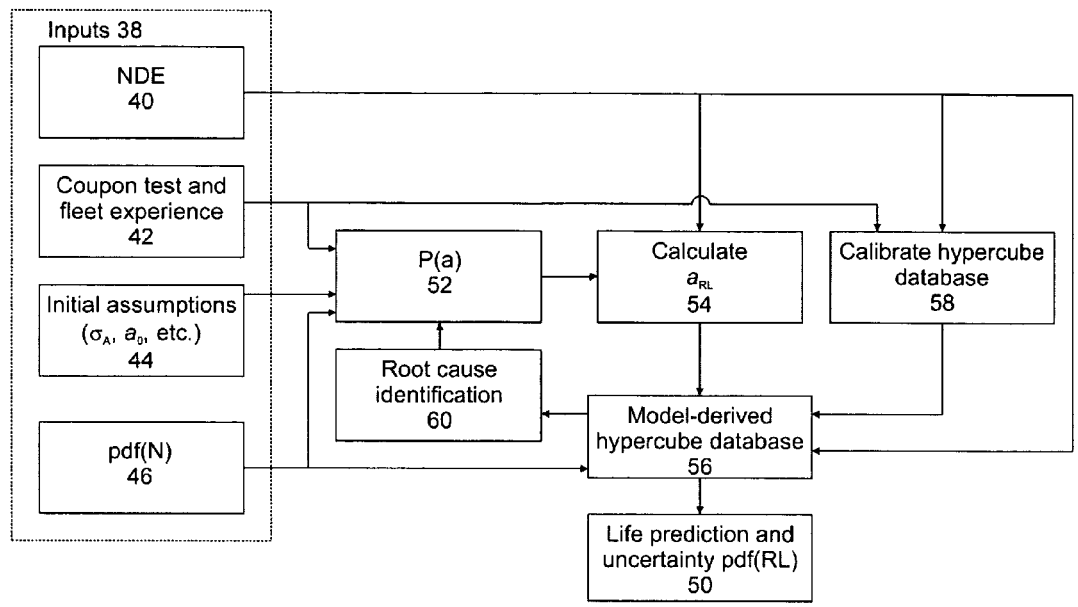
FIG. 3 shows an adaptive asset management framework for rotorcraft dynamic component life management.

To illustrate this approach, FIG. 3 provides a preliminary flow diagram for this adaptive asset management framework specifically for rotorcraft dynamic component life management. The inputs 38 to the framework for coupon and sub-component tests are NDE 40, coupon test and fleet experience 42, initial assumptions for the damage evolution model inputs 44, and the probability density function 46 for the number of cycles N [pdf(N)]. The NDE inputs include conventional crack detection, NDE using MWM-Arrays for discrete crack detection, and digital maps of early damage using MWM-Arrays for microcrack mapping. The output of the NDE is an indication vector, $\hat{i}(\hat{a},\hat{e},\hat{s})$, which is a vector of damage indicators, including crack depth, $\hat{a}$, early damage, $\hat{e}$, and susceptibility to crack initiation, $\hat{s}$, along with the probability that there is no indication, which is the probability of missing a crack of a given size and equal to (1−POD), where POD denotes the probability of detection. The coupon test and fleet experience results can be in the form of documented crack evolution and early damage evolution behavior. The initial assumptions for the damage evolution model inputs can include a later-stage crack propagation model, as well as an early damage initiation and evolution model.

These inputs are used to make a remaining life prediction 50 and determine the uncertainty in the distribution, typically as a probability density function of remaining life [pdf(RL)]. This is accomplished with different combinations for the inputs. For example, these inputs are used to determine the probability of having a crack of depth a [P($\alpha$)] 52 and the remaining life crack size ($\alpha_{RL}$) 54, which in turn is passed through the damage evolution model derived hypercube database 56 to enable the remaining life prediction 50. Note that this damage evolution model may simply represent later-stage crack growth, but it can also be augmented to include models of crack initiation and microcrack cluster growth. Similarly, calibration 58 of the damage evolution hypercube database uses results of coupon tests on the same material as the component of interest with the same NDE/MWM-Array digital mapping procedures, but can also be supported by continuous monitoring with permanently-mounted MWM-Arrays. The precomputed databases are calibrated by either rescaling or adaptation of model inputs, such as the initial crack size, surface finish, or residual stress. This approach also enables identification of root causes 60 of early damage evolution including residual stress relaxation, excessive loads, and surface finish variations, for example from dings, scratches, and fretting. This includes the use of the indication vector to provide a basis for the multivariate inverse determination of the root cause of damage evolution, where these indications are measured at repeated times during the early stage damage evolution prior to the formation of cracks detectable with conventional NDE methods.

Figure 4:
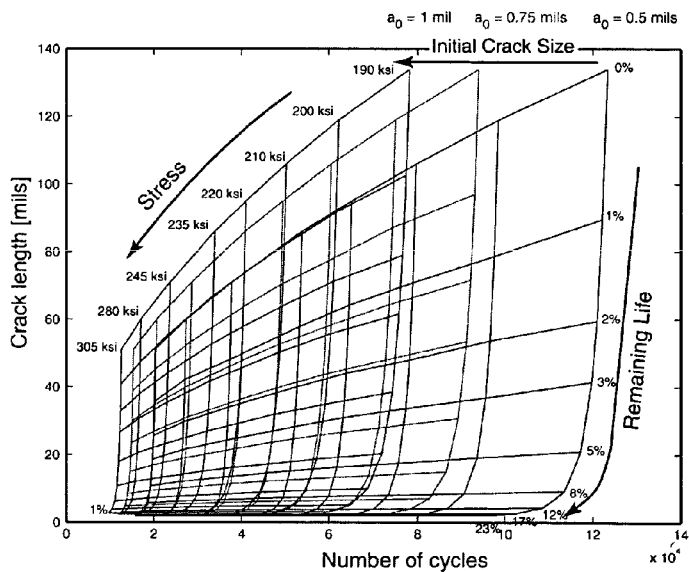
FIG. 4 shows an illustration of a model derived precomputed database for use in the adaptive asset management framework.

At the center of this methodology is the use of model-derived precomputed databases such as that shown in FIG. 4. The use of this lattice is illustrated later in the coupon test results. This lattice was generated for fatigue damage in a titanium alloy and focused on the fatigue damage regime which precedes detectable crack formation (i.e., <0.005-in. depth). While a model for this regime, including microcrack formation and crack coalescence, can be used, a fracture mechanics based damage model for an isolated crack was used for the purposes of this example. In this model, damage is represented as crack depth $\alpha$, even for crack depth considerably below the detection limit, where $\alpha$ may no longer represent a well-defined physical crack, but a "damage state".

The number of cycles $N_i$ to reach damage state $\alpha_i$ is then given by the integrated Paris equation $$N_i = \int_{a_0}^{a_i} \frac{1}{C \cdot \Delta K^n} da$$

where C and n are material-specific constants and $\Delta K$ is the effective stress intensity factor. For the pre-crack regime, including defects or crack nuclei, the simple formulation for damage estimates, namely $\Delta K = \sigma_{max} \cdot (\pi \alpha)^{1/2}$ is used here. We recognize that the Paris equation applies to Stage II growth of "long" cracks, but we used it here for earlier stages of fatigue damage for demonstration purposes. Once a crack has reached measurable dimensions, crack growth calculations can be made, e.g., with the Forman-Newman-de Koning (FNK) model. From these calculations and knowledge of the fracture toughness, the critical crack length for failure, $\alpha_c$, and hence the number of cycles to failure, from detectable crack length, $\alpha_{dl}$, to final crack length $\alpha_c$, can be estimated.

The total number of cycles to failure, $N_f$, consists of two parts, $N_{dl}$ (number of cycles to produce a detectable crack of length $\alpha_{dl}$) and $N_2$, (number of cycles from detectable crack length to failure), $N_f = N_{dl} + N_2$, or, in integral form $$N_f = \int_{a_0}^{a_{dl}} \frac{1}{C \cdot (\sigma \sqrt{\pi a})^n} da + \int_{a_{dl}}^{a_c} \frac{(1-R)^n \left[1 - \frac{\Delta K}{(1-R)K_c}\right]}{C(1-f)^n \Delta K^n \left(1 - \frac{\Delta K_{th}}{\Delta K}\right)^p} da$$

Here $\Delta K_{th}$ is the threshold stress intensity factor, $\Delta K$ is the effective stress intensity factor range, $K_c$ is the applicable fracture toughness, R the stress ratio $\sigma_{min}/\sigma_{max}$, and p another material constant (~0.25).

For the present, case we model a crack originating at the surface of a 0.25-in. diameter hole in a titanium alloy coupon. A simplified assumption for the crack growth relationship is used, namely:

$$N_{sn}(\sigma_n, a_i) = \int_{a_0}^{a_i} \frac{1}{C\left(K_t \sigma_n \sqrt{\frac{\rho}{\rho + 4a}} \sqrt{\pi a}\right)^n} da$$

Figure 5:
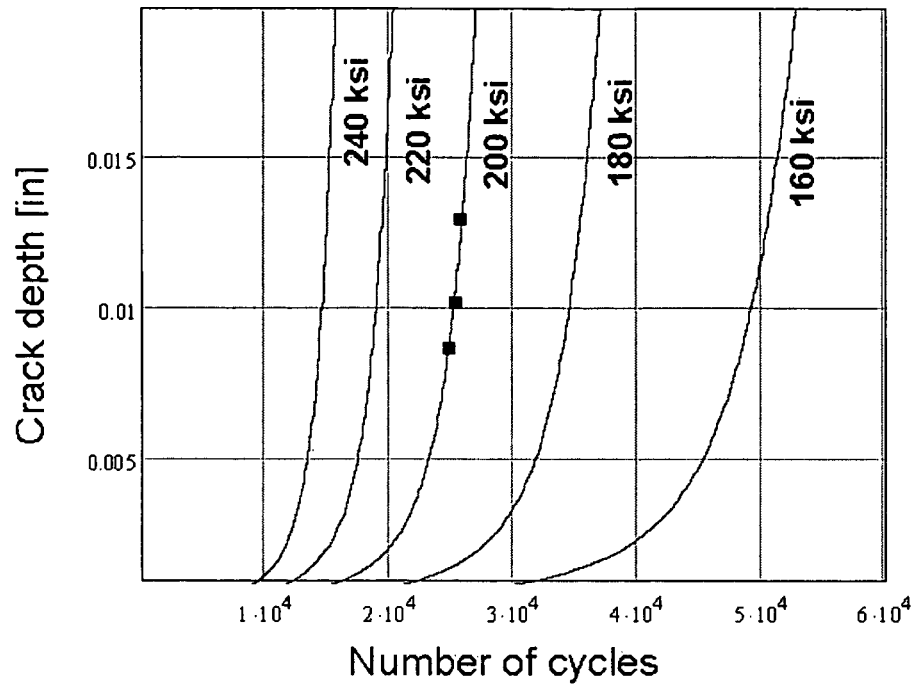
FIG. 5 shows crack growth or "damage" curves for various loads, with $\alpha_0=0.173\text{mils}=0.000173\text{-in}$.
Figure 16:
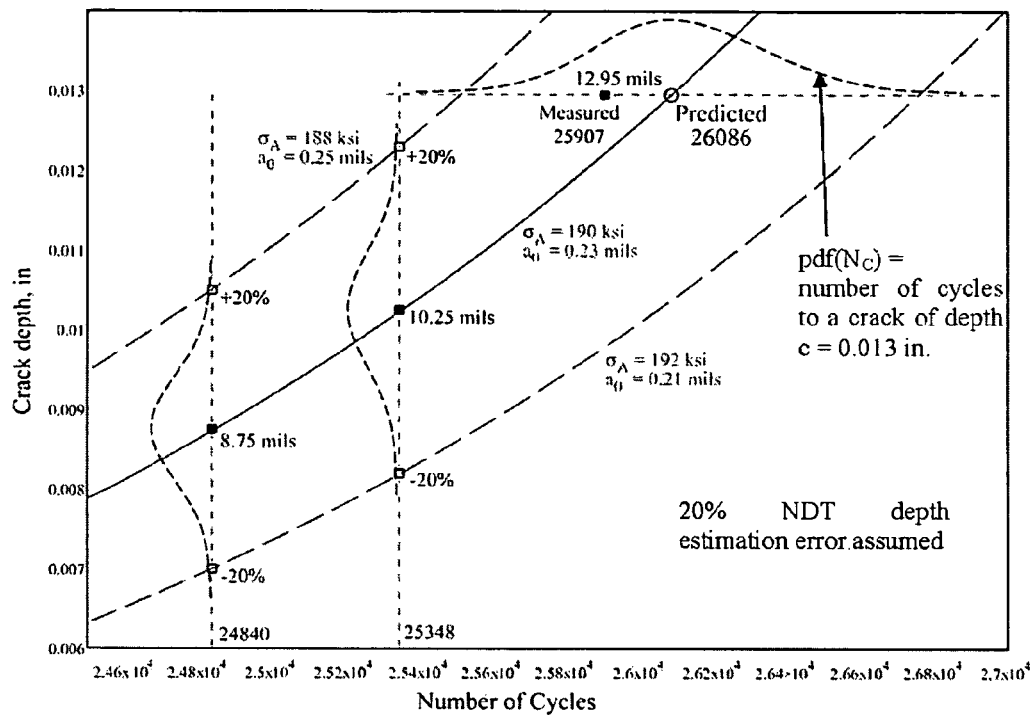
FIG. 16 shows an expanded view of FIG. 15, including results from replicas and the predicted remaining life to reach a prescribed crack size.

Here $K_t$ is the elastic stress concentration factor for the hole geometry, $K_t$~2.4 for the coupon geometry considered here, and $\rho$ is the radius of the hole. Crack growth or "damage" curves for various loads are shown in FIG. 16. FIG. 5 also shows the experimental results from the coupon test with the polished holes (Coupon # 1, described later). The data fit the 200 ksi net section maximum local stress curve when an $\alpha_0$ value of 0.000173-in. is assumed.

Figure 6:
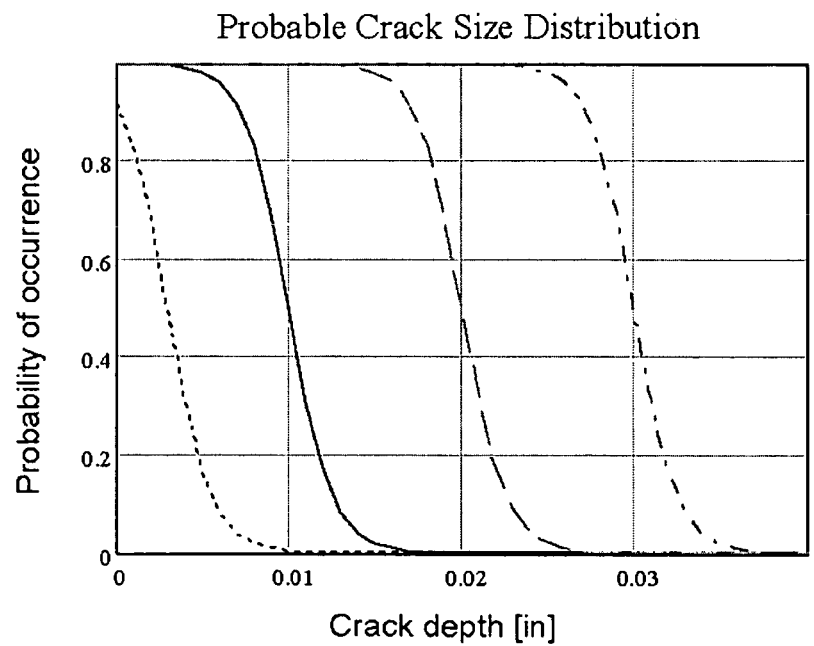
FIG. 6 shows illustrate the probability that a crack of a particular size exists. The sigmoid distribution is used here for illustration purposes and specific distributions can be derived empirically from coupon data and data from the fleet.

If the probability of detection of a crack as a function of crack size (POD($\alpha$)), and the probability of existence of a crack below that detected POC($\alpha$) are known, estimates of missing a crack of a given size can be made. For a hypothetical probable crack size distribution, given the average crack size present is $\alpha_m$, a sigmoid-type distribution is suggested, $$pfd(a) = \frac{1}{e^{\beta(a-a_m)} + 1}$$

and shown in FIG. 6 for $\beta=800$ and various $\alpha_m$ values.

As part of the illustration of the fatigue life prediction methodology, a number of fatigue coupon tests were performed. Two test coupons having a pair of holes are described here. The second coupon test included multiple digital mapping steps with an eddy current sensor array (MWM-Array). In these two tests, flat Ti-6Al-4V coupons (identified here as Coupon #1 and Coupon #2) containing two ¼-in. diameter holes were subjected to cyclic loading at a constant cyclic stress range and R=0.1 in a low-cycle fatigue regime. The material was in the annealed condition. The two coupons used in these fatigue tests were similar, except for the surface finish inside the holes: the coupon used in the first test had as-machined holes, whereas the coupon used in the second fatigue test had polished holes.

The tests were designed for a reasonably short duration (2 to 4 hours) to provide an opportunity for intermittent nondestructive examinations using scanning MWM-Arrays and acetate replicas. The nominal stress range in the net section was approximately 69 ksi. The local stress range at the surface in the highest stress locations within the holes (3 and 9 o'clock positions) was estimated to be 146 ksi, based on the stress concentration factor corrected for notch sensitivity under cyclic loading ($K_t$=2.40 and $K_f$=2.25 for the holes in the titanium coupon). Note that the difference in estimated local stresses here and elsewhere in this report is due to the difference in the elastic stress concentration factor, $K_t$, and the $K_f$ factor. Available data for polished Ti-6Al-4V indicated that the number of cycles to crack "initiation", under such loading should have been somewhere between 10,000 and 20,000 cycles.

A critical crack size from the hole to the front of the crack was estimated using a solution for a through-thickness crack (crack that runs from one face of the flat coupon to the other with a straight front) from D. P. Rooke and D. J. Cartwright, Compendium of Stress Intensity Factors, 1976, pp. 158-159. At the maximum load in the fatigue tests and an assumed fracture toughness value of 50 ksi√in., the estimated crack size is about 0.06-in. For a semicircular or semielliptical crack, the critical size (depth) would be somewhat deeper. Note that solutions for such cracks are available and these solutions should be considered when a more accurate estimate of the critical crack size for bolt holes is required. Also, even with the solution used here, the critical size for a straight front crack becomes approximately 0.12-in., if the fracture toughness is 60 ksi√in., a possible toughness value for annealed T-6Al-4V. Assuming the estimated critical crack size for a semicircular crack (realistic crack shape for cracks at the hole, when a crack has not reached the flat faces) is the same as estimated above, an estimated length, l, at the surface for a critical size crack would be between 0.12 and 0.24-in., depending on the actual fracture toughness. Thus, under the loading conditions prescribed for the test, stable crack growth would be expected at least at l<0.12-in. and possibly l<0.24-in.

For these tests, measurements were performed with Meandering Winding Magnetometer (MWM®) arrays (MWM-Arrays). These arrays provide a "planar," conformable eddy-current sensing capability and were designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). MWM-Arrays can be used for a number of applications, including fatigue monitoring and inspection of structural components for detection of flaws, degradation and microstructural variations as well as for characterization of coatings and process-induced surface layers. a Detailed descriptions of these arrays are given, for example, in U.S. Pat. Nos. 5,453,689, 5,793,206, 6,188,218, and 6,784,662, the entire teachings of which are incorporated herein by reference. Characteristics of these sensors and sensor arrays include directional multi-frequency magnetic permeability or electrical conductivity measurements over a wide range of frequencies, e.g., from 250 Hz to 40 MHz with the same MWM-Array, high-resolution imaging of measured permeability or conductivity, rapid permeability or conductivity measurements with or without a contact with the surface, and a measurement capability on complex surfaces with a hand-held probe or with an automated scanner.

For the two hole coupon tests, FA75 MWM-Arrays are mounted inside the two holes. At three times during the test, the FA75 MWM-Arrays were removed from the holes and MWM-Array scans were acquired using an FA43 scanned over the inside surface of the hole. In this coupon type, the surface of the hole can be either as-machined or polished. For the second test, the holes were polished so that acetate replicas could be used to verify the crack size at the times that NDT was performed. Based on the differences in the trajectories for the normalized conductivity variation with percent of fatigue life, the surface finish may be determined. This also provides an example illustration for root cause identification, in which the relatively rapid reduction in conductivity is cause by the hole not being polished.

Figure 7:
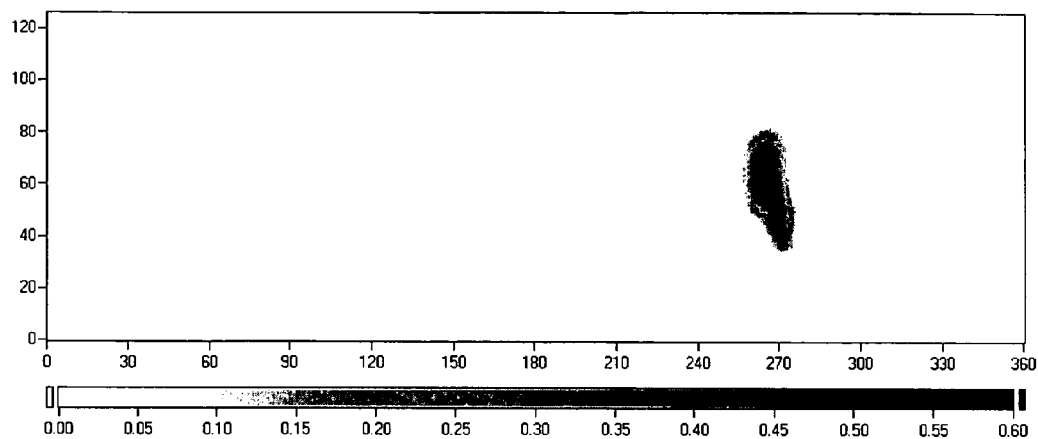
FIG. 7 shows a representative scan image at 12.58 MHz for a crack produced in a fatigue coupon with polished holes. This image was taken at 24,840 cycles and the crack was measured using acetate replicas to be 0.018-in; long and 0.009-in. deep.
Figure 8:
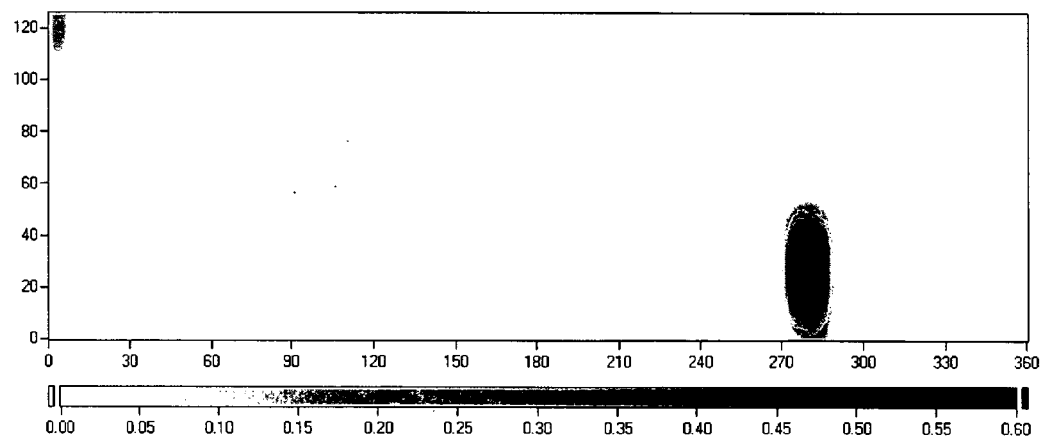
FIG. 8 shows a representative scan image, similar to FIG. 7, but taken at 25,907 cycles. The crack was measured using acetate replicas to be 0.026-in. long and 0.013-in. deep
Figure 9:
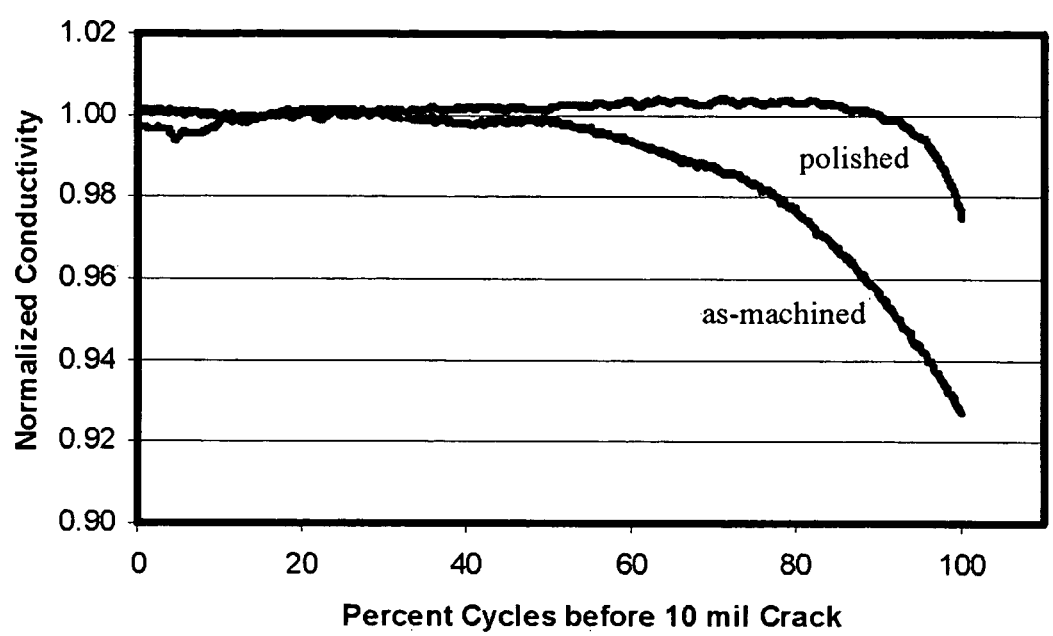
FIG. 9 shows damage progression of cracks on an as-machined and a polished coupon.

FIG. 7 and FIG. 8 show examples of the FA43 digital imaging data for the polished hole Ti-6Al-4V coupon along with micrographs of the acetate replicas taken at different stages of crack growth. For these images, the scan height was 0.247-in. and the scan width represents the angular position around the hole. FIG. 9 shows a comparison between the behavior of the two tests performed for polished and unpolished conditions. To enable this comparison, the effective property data for each coupon test are plotted as a function of the percentage of the number of cycles (in each test) needed to reach a crack depth of 0.01-in. As shown in FIG. 9, early stage damage will be more easily detected when multiple small cracks initiate, which occurs in as-machined titanium, older aluminum alloys, and during bending fatigue.

Figure 10:
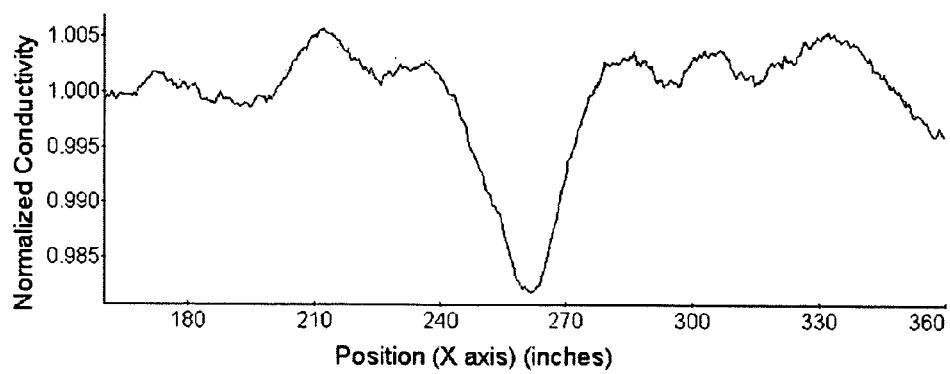
FIG. 10 shows an extracted crack signature used for conductivity image filtering.
Figure 11:
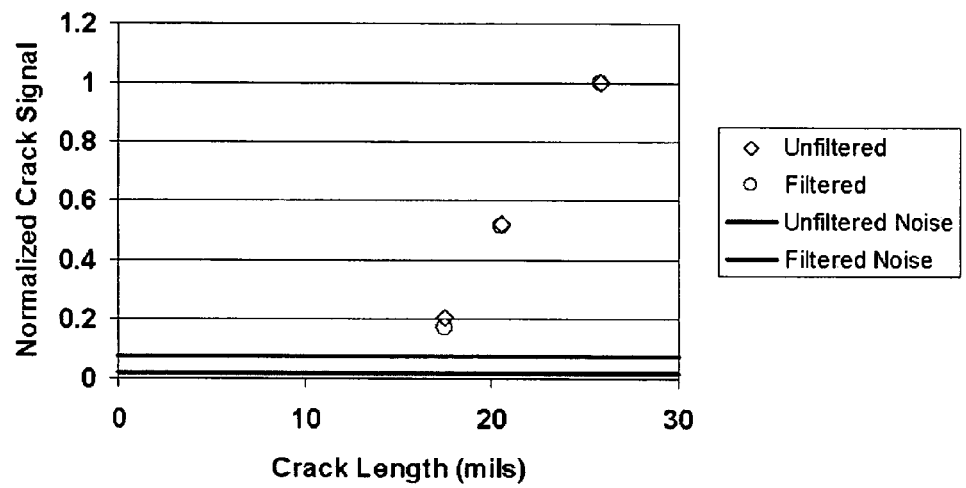
FIG. 11 shows a signal-to-noise comparison for the polished hole coupon test results.

FIG. 10 shows a representative effective conductivity scan versus position for one channel of the MWM-Array. The shape of the response curve can be used as a filter to search the data for similar shapes and to highlight the presence of a crack. The shape filtering of data is described, for example, in U.S. Pat. No. 6,784,662 and U.S. patent application Ser. No. 10/345,883, filed Jan. 15, 2003 and Ser. No. 11/229,844, filed Sep. 19, 2005, the entire contents of which are incorporated herein by reference. FIG. 11 shows a correlation between the normalized crack signal data (obtained at 3.162 MHz) and the crack length. The filtering reduces the background noise for the measurement while leaving the crack signal essentially unchanged. Thus, the application of the shape filtering has the effect of enhancing the crack signal-to-noise ratio.

Two additional fatigue tests were performed on coupons with exposed fatigue-critical surfaces to study the effects of various surface conditions such as surface finish, shot-peening, scratches, dings, etc. In this case, the focus was on the effects of surface dings, for example from foreign object damage. As with the two-hole coupons, fatigue test monitoring was performed with mounted sensors and intermittent scanning of the fatigue-critical regions was also performed. In this case, the FA75 MWM-Arrays were mounted on both "notch" surfaces. The first fatigue test (Coupon #3) was terminated after detection of a surface-connected crack that had grown off one of the lighter dings. The second fatigue test (Coupon #4) was interrupted several times. After each interruption, the FA75 MWM-Arrays were removed from the coupon and MWM-Array FA43 scans were made of the fatigue-critical surfaces.

Material certificates for the Ti-6Al-4V used for these tests indicate that the yield strength is 135-140 ksi and its tensile strength is 147-151 ksi. The coupons were fabricated by milling, and the surface finish in the fatigue critical region was approximately 16 µin. To simulate flaws that might occur on the surface of a component, "dings" were imparted on the coupons in the fatigue critical region. These dings were created using a spring-loaded center punch, and were located at the bottom of the notch radius on each side of the coupon along its centerline. Two ding sizes were achieved in the coupons by adjusting the tension in the center punch, denoted as a "heavy" ding and a "light" ding. The heavy dings were about 0.040-in. across and at least 0.008-in. deep, and the light dings were about 0.032-in. across and approximately 0.004-in. deep.

Baseline scans of the coupons in the "as-dinged" condition were performed with an MWM-Array FA43 sensor. After performing baseline scans, the coupons were cyclically fatigued at a peak load of 20,000 lbs and a minimum load of 400 lbs, for an R value of 0.02. During the fatigue cycling, MWM-Array FA75 sensors were mounted on both sides of each coupon in the fatigue critical regions to continuously monitor local effective conductivity.

Note that the permanently mounted FA75 sensor was calibrated using air/shunt calibration only once, i.e., before the start of the fatigue tests. The Coupon #4 test started on a Friday and was completed the following Tuesday; yet no recalibration of the sensor itself was required throughout the entire test. The scanning FA43 sensor was calibrated using a reference part calibration.

An FA75 MWM-Array was positioned over each area with a ding. Six sense elements from each linear array were monitored during the test, with the two center sense elements positioned over either side of the ding. During fatigue testing of Coupons #3 and #4, data was acquired every 4 seconds. There were 48 measurements per set which spanned 2 fatigue cycles. The frequency of fatigue cycling was 1.5 Hz. Therefore, each set is 6 cycles apart.

Figure 12:
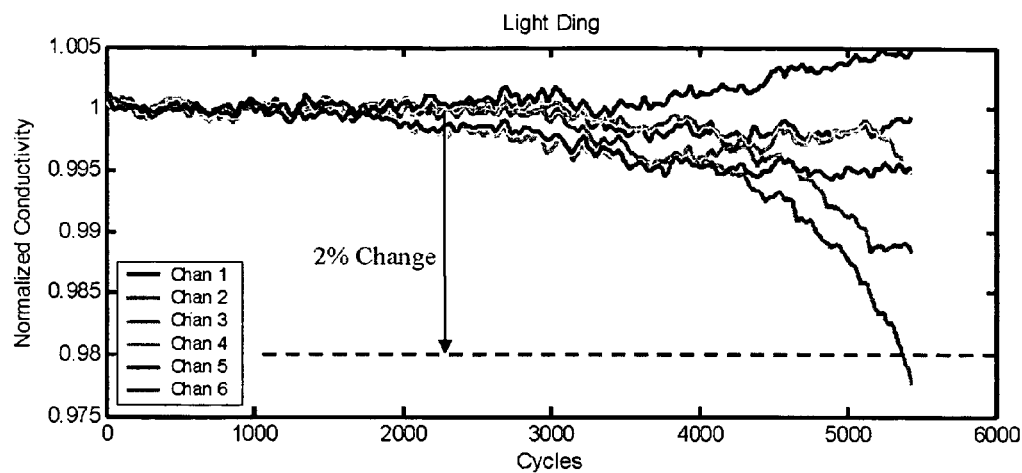
FIG. 12 shows normalized conductivity data acquired during fatigue cycling of Coupon #4 for the light ding region.
Figure 13:
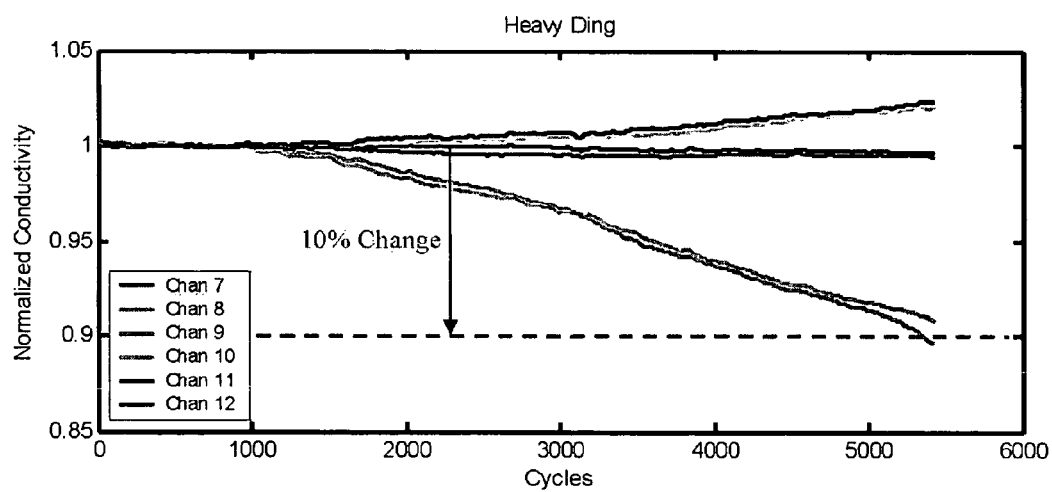
FIG. 13 shows normalized conductivity data acquired during fatigue cycling of Coupon #4 for the heavy ding region.

FIG. 12 and FIG. 13 show normalized conductivity data acquired during fatigue cycling of Coupon #4 with the permanently mounted FA75 sensor for the light ding and heavy ding regions, respectively. In both cases, the normalized conductivity drops first for the sense element channels that are positioned over the edges of the dings. After 1643 cycles in the test of Coupon #4, a change in the effective conductivity was detected at the location of the heavy ding, indicating the formation of a crack. At this point, the test was stopped and the sensors were pealed off of the coupon. A few times through the test, under a full load of 20,000 lbs, acetate replicas were taken of the fatigue critical region to provide photomicrographs of the cracks. Both the coupon and replicas were examined under an optical microscope, and both sides of the coupon were scanned again with the FA43 sensor. Following these examinations, the FA75 sensors were remounted on the coupon, and the fatigue cycling was continued for a number of cycles, during which time a further drop in conductivity was observed with the FA75 sensor at the location of the heavy ding. The fatigue cycling was stopped, and the optical and FA43 scanning examinations were repeated. This sequence of incremental cyclic loading followed by examination was repeated five more times until the crack was visible by optical examination of the coupon and the acetate replica. At the completion of the Coupon #4 test and these examinations, the coupon was cut with a hacksaw on both sides away from the dings, and pulled apart for fractography analysis.

Figure 14:
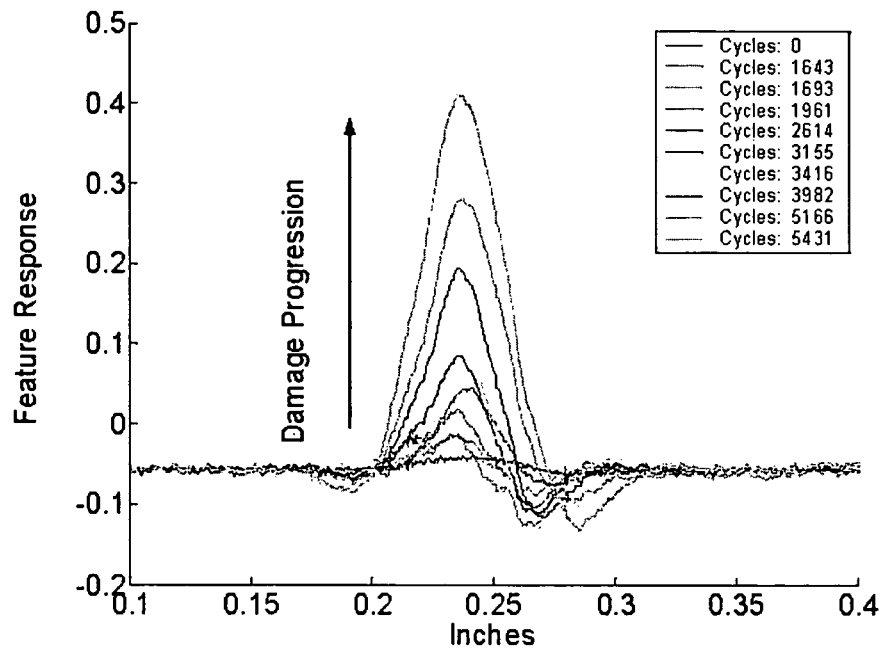
FIG. 14 shows progression of fatigue damage at the heavy ding captured by the scanning MWM-Array.

Cracks were detected by the permanently mounted sensors and the scanning sensors well before they could be revealed optically, either by direct examination of the coupon surface or by examination of the replicas, including replicas taken on the loaded coupon to ensure that the cracks are open. FIG. 14 shows the progression of fatigue damage captured by the corrected B Scans at the heavy ding in Coupon #4. The corrected data was obtained by subtracting scan data acquired after fatigue cycling from the baseline signature data collected prior to any fatigue cycling. More sophisticated methods using spatial filters can also be used to enhance the flaw response.

Cracks in Coupon #4 initiated subsurface at the bottom of a ding. In the heavy ding region, the crack propagated subsurface over a major part of the fatigue life and eventually grew to the surface surrounding the ding. In the light ding region, the crack barely reached the surface (0.001-in. off of the ding), yet both the permanently mounted and scanning MWM-Arrays detected the subsurface crack early in fatigue life, well before the crack reached the surface. This capability of the MWM-Arrays to detect early fatigue damage and track it throughout fatigue life, both with permanently mounted and scanning arrays was confirmed with optical examinations of the light and heavy ding regions.

Fatigue life uncertainty in the presence of local indentations, e.g., dings, is affected by a number of factors such as (1) geometry of the ding (which affects the local stress concentration), (2) local residual stresses at the ding induced or redistributed by the impact that created the ding, (3) local microstructural damage, and (4) possible strengthening from local deformation at the impact site. Each of these factors contributes to the uncertainty. For example, the stress concentration factor alone can vary widely depending on details of the ding geometry and, thus, would significantly affect estimates of fatigue life. Thus, early detection of fatigue damage in a component, including fatigue damage at small dings, combined with damage mapping and tracking capability becomes essential for component life management.

Figure 15:
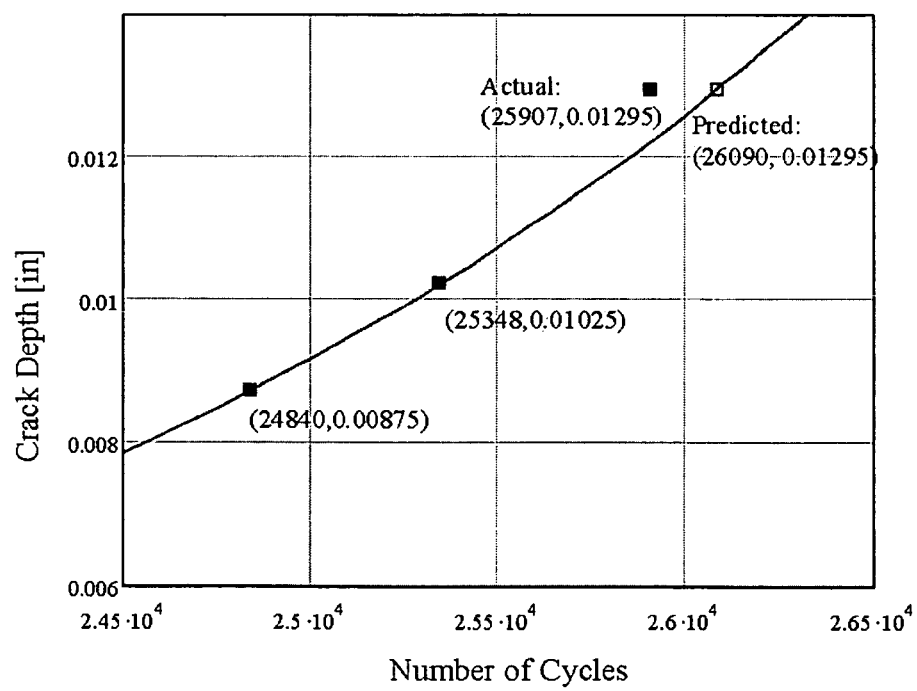
FIG. 15 shows the modeled response for crack depth evolution with number of cycles.

Rapid assessment of fatigue damage and remaining life prediction can be accomplished using the precomputed databases of responses. FIG. 15 and FIG. 16 provide an illustration of remaining life prediction for Coupon #2. In FIG. 16, the actual crack sizes determined from the replicas are used to calibrate the model. The model is then used to predict the number of cycles to reach a prescribed crack size of 0.013-in. depth. FIG. 16 also shows the effect of uncertainty in the MWM-Array crack size estimates on the predicted number of cycles to a prescribed crack size. To accommodate this, in this case, the model inputs were varied to produce response curves that match the extremes in the crack size range to produce the distribution for the remaining life. While an assumed error (20% in this case) for the crack depth measurements can be used to determine the extremes in the distribution, it is preferably to use the results of coupon test data to actually determine the appropriate error or distribution.

Figure 17:
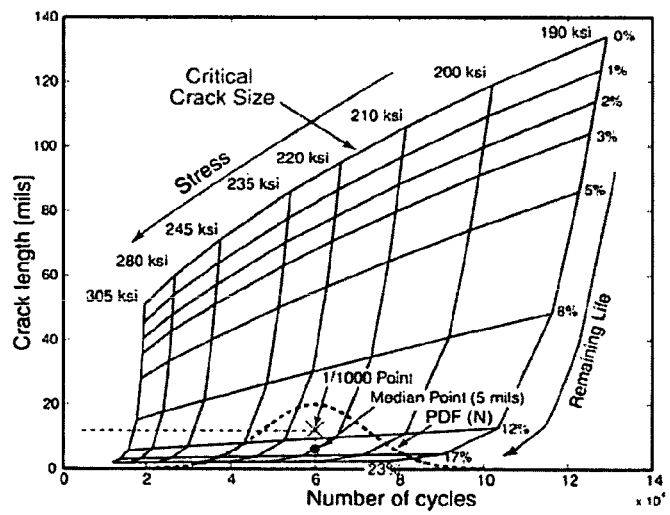
FIG. 17 shows an illustration of a model derived precomputed database relating crack length and the number of cycles to the stress and remaining life.
Figure 18:
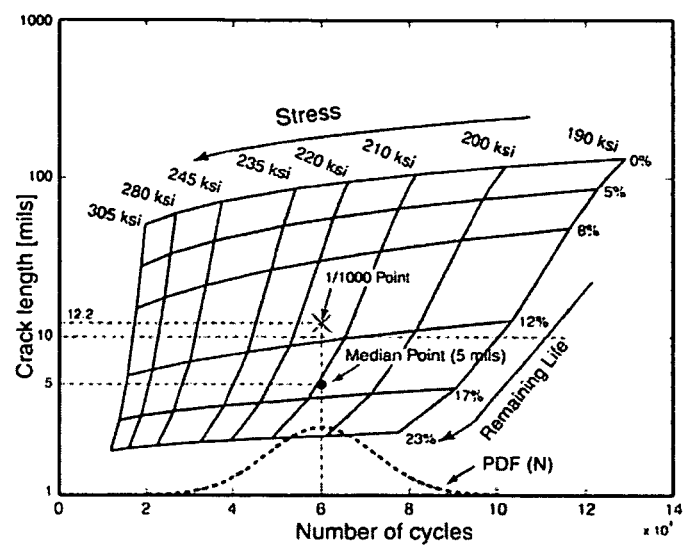
FIG. 18 shows an alternative view of FIG. 17 with the vertical axis plotted logarithmically.
Figure 19:
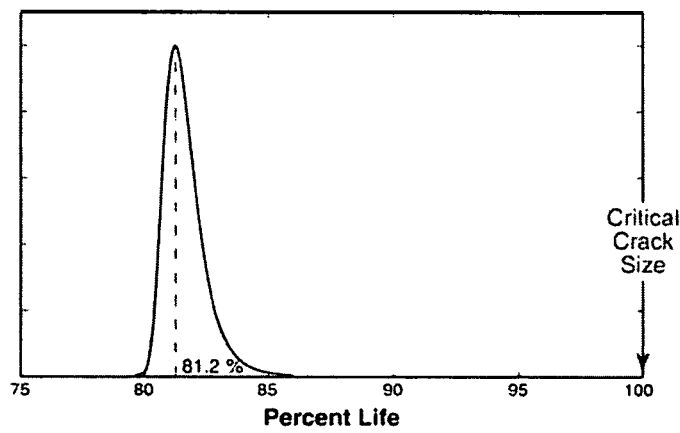
FIG. 19 shows a distribution for the remaining life obtained by mapping the uncertainties through the database hypercube of FIG. 17 for a model input, N, and given the largest crack with a probability $P(a) \geq 1/1000$.

FIGS. 17 to 19 illustrate the use of MWM-Array data for remaining life prediction. For illustration purposes, the functional correlation between conductivity and crack depth was assumed but empirical correlations based on multiple frequency measurements could also be used. This precomputed database driven capability to rapidly estimate uncertainty distributions for a variety of case studies is critical to the decision support framework for adaptive life management of critical dynamic components such as rotorcraft. As shown in FIGS. 17 to 19, in one implementation, the uncertainty in the number of cycles at any point in time can be reflected through the precomputed lattice for a given estimated crack size to predict the remaining life and the associated distribution of the remaining life. In the example shown here, the selected crack size is the largest crack with a 1/1000 probability of existing. This could also be an indicator of early damage with a 1/1000 or other prescribed probability.

Figure 20:
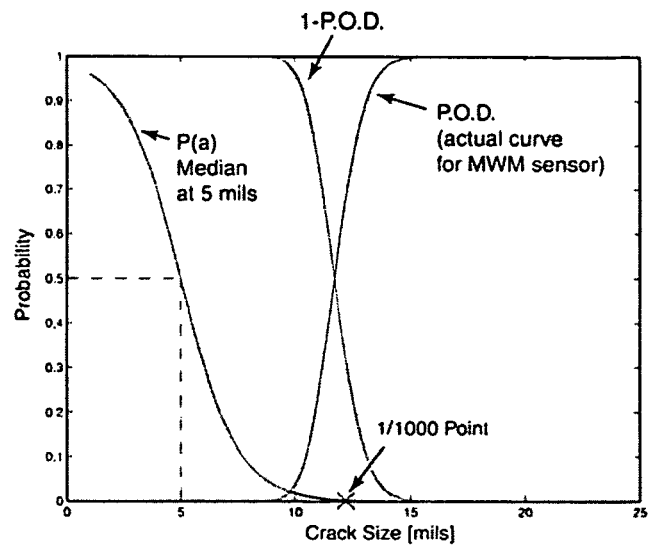
FIG. 20 shows an example P(a) distribution and method for determination of largest crack size with $P(a) \geq 1/1000$. The POD curve used in this example is an actual POD curve for the MWM sensor.
Figure 21:
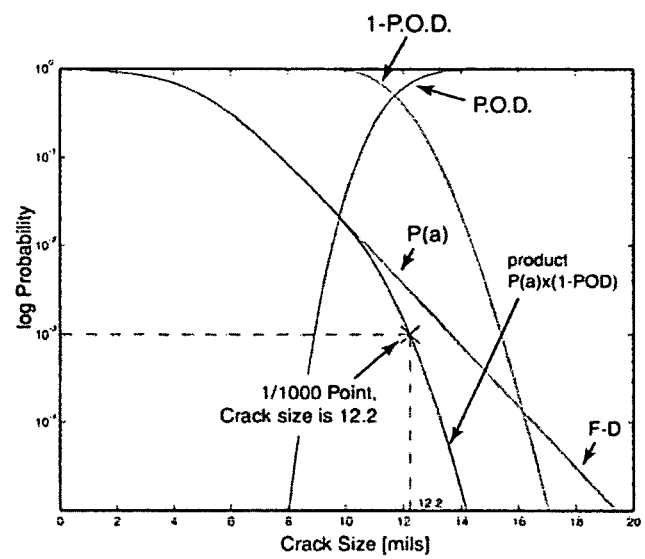
FIG. 21 shows an alternative view of FIG. 20 with the vertical axis plotted logarithmically.

The adaptive asset management framework enables computation of remaining life both interactively and autonomously. FIG. 20 and FIG. 21 illustrate the method used to determine the largest crack size with a 1/1000 probability. POD denotes the probability of detection with an MWM-Array and P(a) denotes the probability of having a crack of depth α without any NDE information. This method combines empirical crack and damage experience with sensor performance statistics (e.g., POD curve) to account for uncertainties. Note that the product P(a) and (1−POD) gives the probability that there is a crack of a given size given no detection with an NDE measurement. Also, a distribution of the type shown in FIG. 6 centered on a 0.005-in. crack was used to obtain the results in FIGS. 17 to 21.

For this approach to be useful the model used to generate or precompute the database must be reasonably accurate. If the model is very accurate, having a predictive accuracy of greater than about 90% for the output value, then a deterministic prediction is typically adequate. Similarly, if its predictive accuracy is less than about 30% of the output value, then it is not useful and other approaches should be used. However, if the predictive accuracy is between about 30% and 90% of the output value, then the combination of the model, the calibration, and quantitative information about the system, such as NDE, provides a useful prediction of future behavior and uncertainties for the system.

It is also worth noting that although the emphasis of the description has focused on damage evolution model, any system having nonlinear behavior that can be modeled reasonably accurately can benefit from this approach. As long as there is measurable quantitative information, which is not necessarily sensor based, that can be passed through the database and even used to calibrate the database, this approach can be used to predict future behavior. For example, if you are running a hedge fund and want to predict if a stock is going to go up or down, you could use quantitative inputs with a precomputed database. Similarly, this methodology or framework can be embedded or incorporated into controllers, particularly for controllers of nonlinear, dynamic systems.

While the inventions have been particularly shown and described with reference to preferred embodiments thereof, it will be understood to those skilled in the art that various changes in form and details may be made therein without departing from the spirit and scope of the invention as defined by the appended claims.

What is claimed is:

1. A method for rapid decision making for a nonlinear system, the method comprising:
providing a database of system responses, the database relating a plurality of input variables to at least one output variable predicting a future state of a component, at least one of the plurality of input variables being a current component damage level, each output variable having a nonlinear dependence on the plurality of input variables;
calibrating the database's relations between the plurality of input variables to the at least one output variable predicting the future state with first empirical information about the nonlinear system;
obtaining a sensor response from a sensor;
estimating a current component damage level probability distribution from the sensor response and second empirical data representing a dependence of the sensor response on the damage level;
inputting the current component damage level probability distribution to a multivariate inverse method;

estimating a future state probability distribution using the database and the multivariate inverse method; and using the future state probability distribution to make a decision.

2. The method as claimed in claim 1 wherein the database is precomputed, using a model for the nonlinear system's behavior, prior to using the database in estimating the future state probability distribution.

3. The method as claimed in claim 1 wherein the inputting comprises inputting the plurality of input variables, including the current component damage level probability distribution, to the multivariate inverse method, and the method further includes dividing the plurality of the measured input variables into portions, determining a weighting value for each portion, and further calculating the future state probability distribution by passing the measured input variables and weighted value of each portion through the database of system responses.

4. The method as claimed in claim 3 wherein calculating the future state probability distribution involves passing a fraction of the plurality of input variables into the database.

5. The method as claimed in claim 4 further comprising using a Latin hypercube methodology to determine the future state probability distribution, by passing a substantially reduced number of inputs through the database to construct the future state probability distribution.

6. The method as claimed in claim 1 wherein the sensor response is obtained using an eddy current sensor.

7. The method as claimed in claim 1 wherein current component damage level probability distribution is crack size.

8. The method as claimed in claim 1 wherein at least one input variable is number of cycles.

9. The method as claimed in claim 1 wherein the future state probability distribution is a distribution of crack sizes at a prescribed number of cycles.

10. The method as claimed in claim 1 wherein the future state probability distribution is a number of cycles required to reach a specific crack size.

11. The method as claimed in claim 1 wherein estimating the current component damage level probability distribution from the sensor response comprises subtracting a baseline response from the sensor response.

12. A method for rapid decision making for a nonlinear system, the method comprising:
generating a database of system responses from a damage evolution model, the database relating a plurality of input variables to at least one output variable predicting a future state of a component, at least one of the plurality of input variables being a current component damage level, each output variable having a nonlinear dependence on the plurality of input variables;
storing the database for future use;
calibrating the database's relations between the plurality of input variables to the at least one output variable predicting the future state with first empirical information about the nonlinear system;
obtaining a sensor response from a sensor;
estimating a current component damage level probability distribution from the sensor response and second empirical data representing a dependence of the sensor response on the damage level;
inputting the current component damage level probability distribution to a multivariate inverse method;
estimating a future state probability distribution using the database and the multivariate inverse method; and
using the future state probability distribution to make a decision.

13. The method as claimed in claim 12 wherein the first empirical information is sensor based.

14. The method as claimed in claim 13 wherein the sensor is an eddy current sensor.

15. The method as claimed in claim 12 wherein a shape of the future state probability distribution is assumed.

16. The method as claimed in claim 12 wherein the future state probability distribution is determined by measurement.

17. The method as claimed in claim 12 wherein the component is a shot peened metal.

18. The method as claimed in claim 1 wherein the sensor response is an image of effective material properties.

19. The method as claimed in claim 12 wherein the component damage level represents a size of a crack in the component.

20. The method as claimed in claim 12 wherein the plurality of input variables comprises a number of cycles the component has been in use.

21. The method as claimed in claim 12 wherein the future state probability distribution is remaining life.

22. The method as claimed in claim 12 wherein the future state probability distribution is a distribution of cycles in which a prescribed crack size is reached and further including determining a decision regarding fitness for service as a function of the distribution of cycles.

23. A method for rapid decision making for a nonlinear system, the method comprising:
providing a database of system responses generated from a model, the database relating a plurality of input variables to at least one output variable predicting a future state of a component, at least one of the plurality of input variables being a measure of temporal usage, at least one of the plurality of input variables being a current component damage level, each output variable having a nonlinear dependence on the plurality of input variables;
calibrating the database with first empirical information about the nonlinear system;
obtaining a sensor response from a sensor;
estimating a current component damage level probability distribution from the sensor response and second empirical information representing a dependence of the sensor response on the current component damage level;
receiving the temporal usage;
inputting the temporal usage and the current component damage level probability distribution to a multivariate inverse method;
estimating a future state probability distribution using the database and the multivariate inverse method; and
using the future state probability distribution to make a decision.

24. The method of claim 23, wherein the temporal usage is a number of cycles a component has been used.

25. The method of claim 23, wherein the temporal usage is a number of hours a component has been used in flight.

26. The method of claim 12, wherein the second empirical data defines a probability of detection for the sensor.

27. The method of claim 12, wherein calibrating the database comprises performing one or more coupon tests to estimate parameters of the damage evolution model used to generate the database.

* * * * *